US012605081B2

(12) United States Patent
Nara et al.

(10) Patent No.:   US 12,605,081 B2
(45) Date of Patent:      Apr. 21, 2026

(54) CUFF FOR BLOOD PRESSURE MEASUREMENT, AND METHOD OF MANUFACTURING CUFF FOR BLOOD PRESSURE MEASUREMENT

(71) Applicant: NIHON KOHDEN CORPORATION, Tokyo (JP)

(72) Inventors: Taku Nara, Tokorozawa (JP); Naoki Ashiba, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 1130 days.

(21) Appl. No.: 17/426,718

(22) PCT Filed: Jan. 7, 2020

(86) PCT No.: PCT/JP2020/000179
§ 371 (c)(1),
(2) Date: Jul. 29, 2021

(87) PCT Pub. No.: WO2020/158303
PCT Pub. Date: Aug. 6, 2020

(65) Prior Publication Data
US 2022/0095941 A1      Mar. 31, 2022

(30) Foreign Application Priority Data
Jan. 31, 2019    (JP) ................................. 2019-015839

(51) Int. Cl.
*A61B 5/022*            (2006.01)
(52) U.S. Cl.
CPC ...... *A61B 5/02233* (2013.01); *A61B 2562/12* (2013.01)

(58) Field of Classification Search
None
See application file for complete search history.

(56) References Cited

U.S. PATENT DOCUMENTS

2005/0240109 A1*  10/2005  Inoue ................. A61B 5/02141
                                                                                        600/490
2006/0027946 A1    2/2006  Kawamura
2010/0010357 A1*   1/2010  Ostrowiecki ...... A61B 5/02233
                                                                                        600/499

FOREIGN PATENT DOCUMENTS

JP          H04-067837 A      3/1992
JP          H05-064631 A      3/1993
JP          H05-154114 A      6/1993
JP          2003-052651 A     2/2003
JP          2008-168157 A     7/2008

OTHER PUBLICATIONS

International Search Report dated Mar. 20, 2021 Issued in Patent Application No. PCT/JP2020/000179.
Written Opinion dated Mar. 20, 2021 Issued in Patent Application No. PCT/JP2020/000179.
Japanese Office Action issued in patent application No. 2019-015839 received on Dec. 13, 2022.

* cited by examiner

*Primary Examiner* — Aurelie H Tu
(74) *Attorney, Agent, or Firm* — McDonald Hopkins LLC

(57)                  ABSTRACT

A sheet member is to form a bladder. A tubular member is to form a ventilation channel communicating with the bladder. A welded portion at which the sheet member and the tubular member are welded extends along a longitudinal direction of the tubular member over an entire circumference of the tubular member.

7 Claims, 7 Drawing Sheets

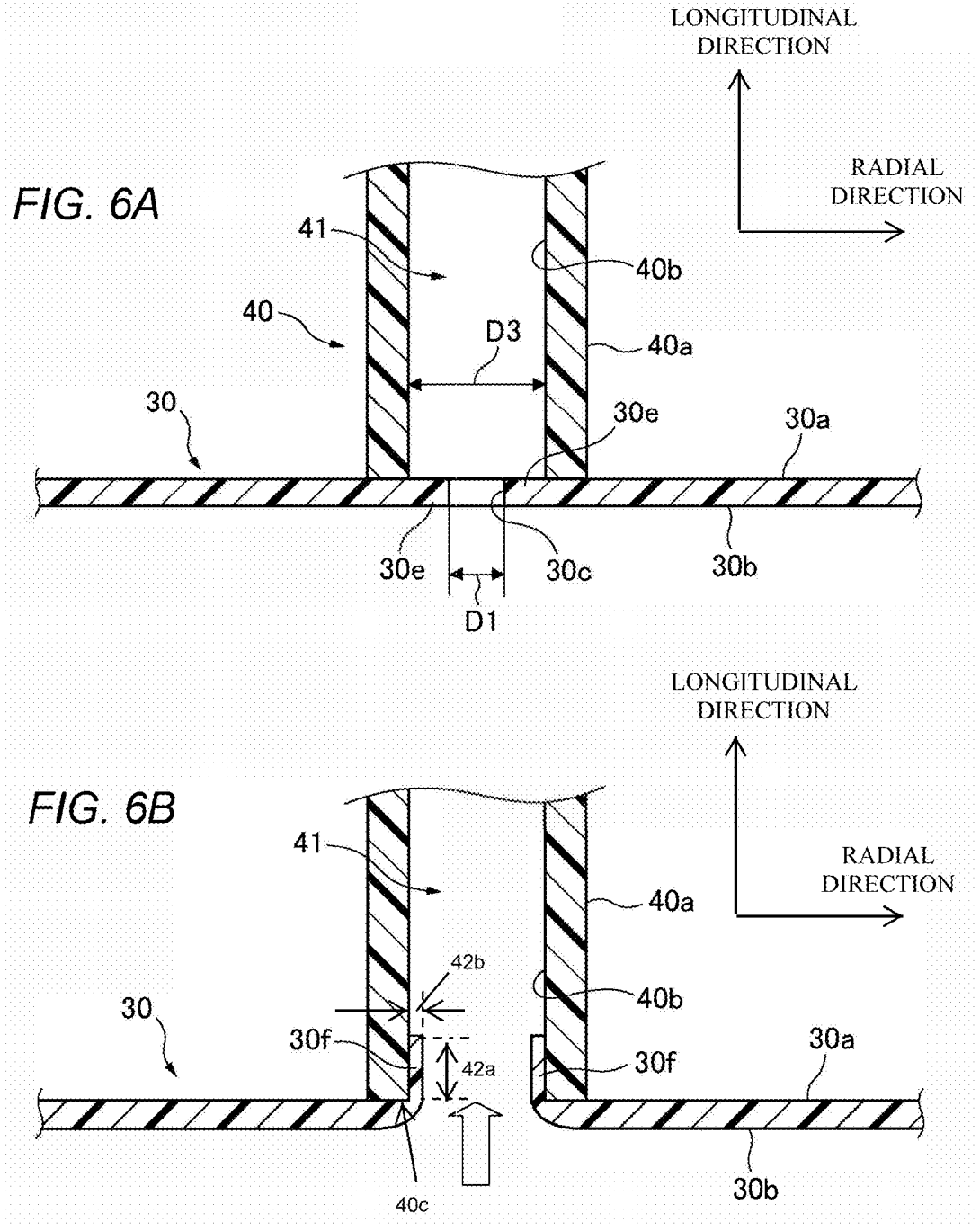

CUFF FOR BLOOD PRESSURE MEASUREMENT, AND METHOD OF MANUFACTURING CUFF FOR BLOOD PRESSURE MEASUREMENT

TECHNICAL FIELD

The presently disclosed subject matter relates to a cuff adapted to be used for non-invasive blood pressure measurement. The presently disclosed subject matter also relates to a method of manufacturing the cuff.

BACKGROUND ART

The cuff adapted to be used for the non-invasive blood pressure measurement includes a bladder and a ventilation tube. The ventilation tube defines a ventilation channel that communicates with the interior of the bladder. In the cuff described in PTL1, a member called a nozzle corresponds to the ventilation tube. The nozzle has a tubular portion defining a ventilation channel and a collar extending radially outwards from the tubular portion.

In manufacturing the cuff described in PTL1, the tubular portion of the nozzle is inserted into a hole formed in a sheet member from the side of a first surface of the sheet member, whereby the tubular portion is exposed to the side of a second surface of the sheet member. Subsequently, a flange portion of the nozzle is welded to the first surface of the sheet member, whereby the sheet member and the nozzle are made integrally indivisible. Thereafter, predetermined portions of the sheet member are welded to each other to form a bladder. The first surface and the second surface of the sheet member become the inner surface and the outer surface of the bladder, respectively.

CITATION LIST

Patent Literature

[PTL1] Japanese Patent Publication No. H04-067837A

SUMMARY OF INVENTION

Technical Problem

In order to accurately measure the blood pressure, it is required that the surface of the cuff is flexibly deformed along the body surface of a subject to maintain the close contact therebetween. However, in the bladder of the cuff described in PTL1, the portion where the flange portion of the nozzle is welded to the sheet member has a larger thickness dimension than other portions, and thus the flexibility is decreased. This may result in a gap between the surface of the cuff and the body surface of the subject because the joint portion of the bladder and the ventilation tube cannot flexibly deform along the shape of the body surface.

Accordingly, it is demanded to suppress the decrease in flexibility at the joint portion between the bladder and the ventilation tube in the cuff.

Solution to Problem

An illustrative aspect of the presently disclosed subject matter provides a cuff adapted to be used for blood pressure measurement comprising:
a sheet member forming a bladder;

a tubular member forming a ventilation channel communicating with the bladder; and
a welded portion at which the sheet member and the tubular member are welded,
wherein the welded portion extends along a longitudinal direction of the tubular member over an entire circumference of the tubular member.

An illustrative aspect of the presently disclosed subject matter provides a cuff adapted to be used for blood pressure measurement comprising:
a cuff adapted to be used for blood pressure measurement comprising:
a sheet member forming a bladder;
a tubular member forming a ventilation channel communicating with the bladder;
a first welded portion at which the sheet member and the tubular member are welded; and
a second welded portion at which different portions of the sheet member are welded,
wherein the first welded portion extends along a longitudinal direction of the tubular member over an entire circumference of the tubular member, and is separated from the second welded portion.

An illustrative aspect of the presently disclosed subject matter provides a method of manufacturing a cuff adapted to be used for blood pressure measurement comprising steps of: forming a hole in a sheet member;
inserting a tubular member, that has a larger outer diameter than a diameter of the hole, through the hole to form a portion extending along a longitudinal direction of the tubular member in the sheet member;
welding the portion of the sheet member that extends along the longitudinal direction of the tubular member to an outer circumferential surface of the tubular member to form a welded portion; and
welding different portions of the sheet member at a position separated from the welded portion to form a bladder that communicates with a ventilation channel defined by the tubular member.

An illustrative aspect of the presently disclosed subject matter provides a method of manufacturing a cuff adapted to be used for blood pressure measurement comprising steps of:
forming a hole in a sheet member;
placing a tubular member, that defines a ventilation channel having a larger inner diameter than a diameter of the hole, in a first side of the sheet member;
pushing a peripheral portion of the hole in the sheet member into the ventilation channel from a second side of the sheet member to form a portion extending along a longitudinal direction of the tubular member;
welding the portion of the sheet member that extends along the longitudinal direction of the tubular member to an inner circumferential surface of the tubular member to form a welded portion; and
welding different portions of the sheet member at a position separated from the welded portion to form a bladder that communicates with a ventilation channel defined by the tubular member.

When the welded portion is formed by a flange portion like the nozzle in the cuff described in PTL1, such a welded portion extends on the inner surface of the bladder along the radial direction of the ventilation tube. According to the configuration of each of the above illustrative aspects, since the formation of such a flange portion is unnecessary, the welded portion (the first welded portion) does not have a portion extending along the radial direction of the tubular member. Accordingly, it is possible to suppress a decrease in flexibility at the joint portion between the bladder and the ventilation tube. As a result, the close contactability between the surface of the cuff and the body surface of the subject can be improved, which can contribute to an improvement in the accuracy of blood pressure measurement.

The second welded portion is formed by welding different portions of the sheet member in a plane orthogonal to the longitudinal direction of the tubular member. In other words, the second welded portion has a large thickness dimension in the plane orthogonal to the longitudinal direction of the tubular member, and thus has low flexibility. Since the second welded portion is separated from the first welded portion forming the joint portion between the sheet member and the tubular member, the influence of the rigidity of the second welded portion on the flexibility of the joint portion can be suppressed. That is, the flexibility of the joint portion between the bladder and the ventilation tube does not have a direction dependence in the plane orthogonal to the longitudinal direction of the ventilation tube. As a result, the degree of freedom of deformation at the joint portion between the bladder and the ventilation tube is improved. Therefore, the close contactability between the surface of the cuff and the body surface of the subject can be improved, which can contribute to the improvement of the accuracy of the blood pressure measurement.

In order to manufacture a component having a flange portion such as the nozzle in the cuff described in PTL1, injection molding is necessary. On the other hand, since the tubular member according to each of the above illustrative aspects does not have such a flange portion, it can be manufactured by extrusion molding. Since the extrusion molding is a lower-cost method than the injection molding, an increase in the manufacturing cost of the cuff can be suppressed.

BRIEF DESCRIPTION OF DRAWING

FIG. 6A illustrates another method of manufacturing the cuff

FIG. 6B illustrates another method of manufacturing the cuff.

DESCRIPTION OF EMBODIMENTS

Examples of embodiments are described in detail below with reference to the accompanying drawings. In each of the drawings, the scale is appropriately changed in order to make each element to be described have a recognizable size.

Figure 1A:
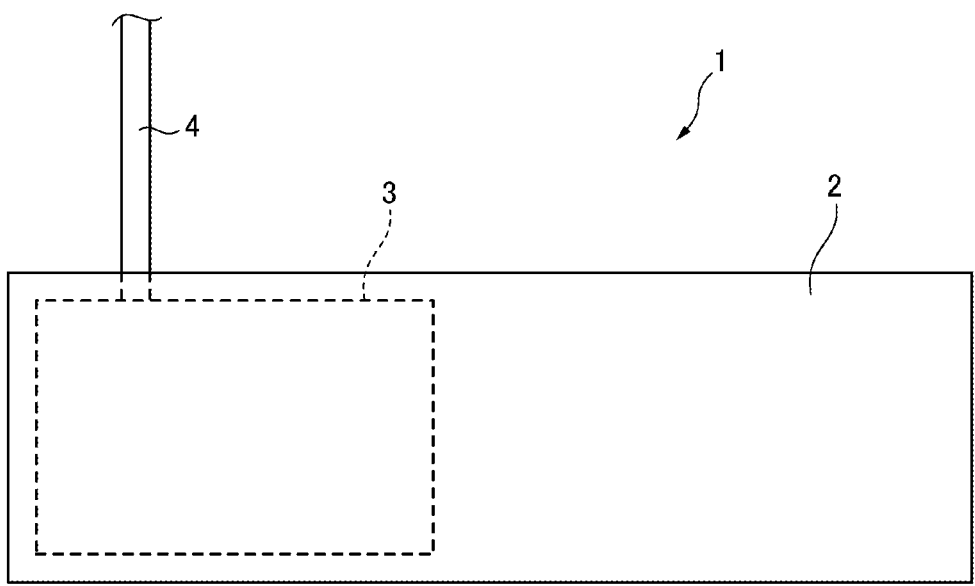
FIG. 1A illustrates an external appearance of a cuff according to an embodiment.
Figure 1B:
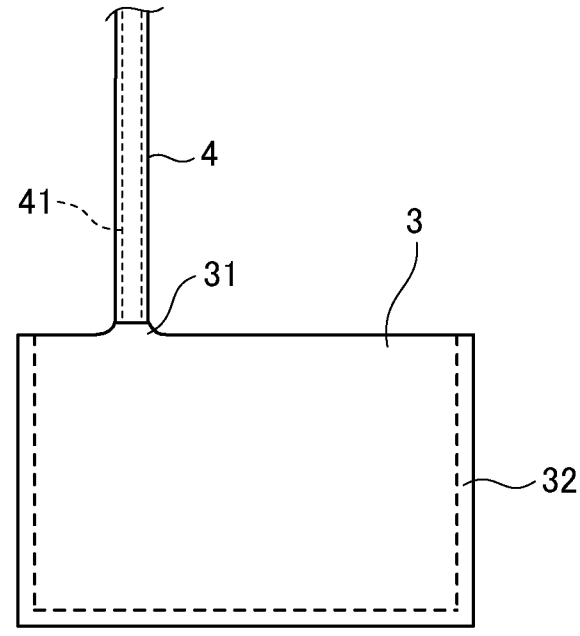
FIG. 1B illustrates an external appearance of a portion of the cuff.

FIG. 1A illustrates an external appearance of a portion of a cuff 1 according to one embodiment. The cuff 1 is adapted to be used for the non-invasive blood pressure measurement. The cuff 1 comprises an arm band 2, a bladder 3 and a ventilation tube 4. The 1B illustrates an external appearance of the bladder 3 and an external appearance of a portion of the ventilation tube 4.

The arm band 2 is adapted to be wound around an upper arm of a subject. The bladder 3 is incorporated in the arm band 2. The bladder 3 is formed of a sheet member having elasticity. As the material of the sheet member, a thermoplastic elastomer can be exemplified.

The ventilation tube 4 defines a ventilation channel 41 communicating with the interior of the bladder 3. When air is supplied from a pump (not illustrated) to the bladder 3 through the air passage 41, the bladder 3 expands so that the upper arm of the subject is pressurized through the arm band 2. When air is discharged from the bladder 3 through the ventilation channel 41, the bladder 3 contracts so that the pressurization state is canceled.

The bladder 3 has a first welded portion 31 and a second welded portion 32. The first welded portion 31 is a portion which is made integrally indivisible by welding a portion of the bladder 3 and a portion of the ventilation tube 4. The second welded portion 32 is a portion which is made integrally indivisible by welding different portions of the sheet member. The first welded portion 31 and the second welded portion 32 define the bladder 3 having airtightness. The first welded portion 31 and the second welded portion 32 are separated from each other.

The first welded portion 31 extends in the longitudinal direction of the ventilation tube 4 over the entire circumference of the ventilation tube 4. As will be described later, the first welded portion 31 is a portion which is made integrally indivisible by welding a portion of the sheet member for forming the bladder 3 and a portion of a tubular member for forming the ventilation tube 4. Therefore, when viewed microscopically, the first welded portion 31 has a three-dimensional expansion. As used herein, the expression "the welded portion extends in the longitudinal direction of the tubular member" means that the dimension $42a$ of the welded portion along the longitudinal direction of the tubular member is greater than the dimension $42b$ of the welded portion along the radial direction of the tubular member. Alternatively, it means that the dimension of the welded portion along the radial direction of the tubular member is negligibly small compared to the dimension of the welded portion along the longitudinal direction of the tubular member.

An example of a method of manufacturing the cuff 1 having such a configuration will be described with reference to FIGS. 2 to 5.

Figure 2:
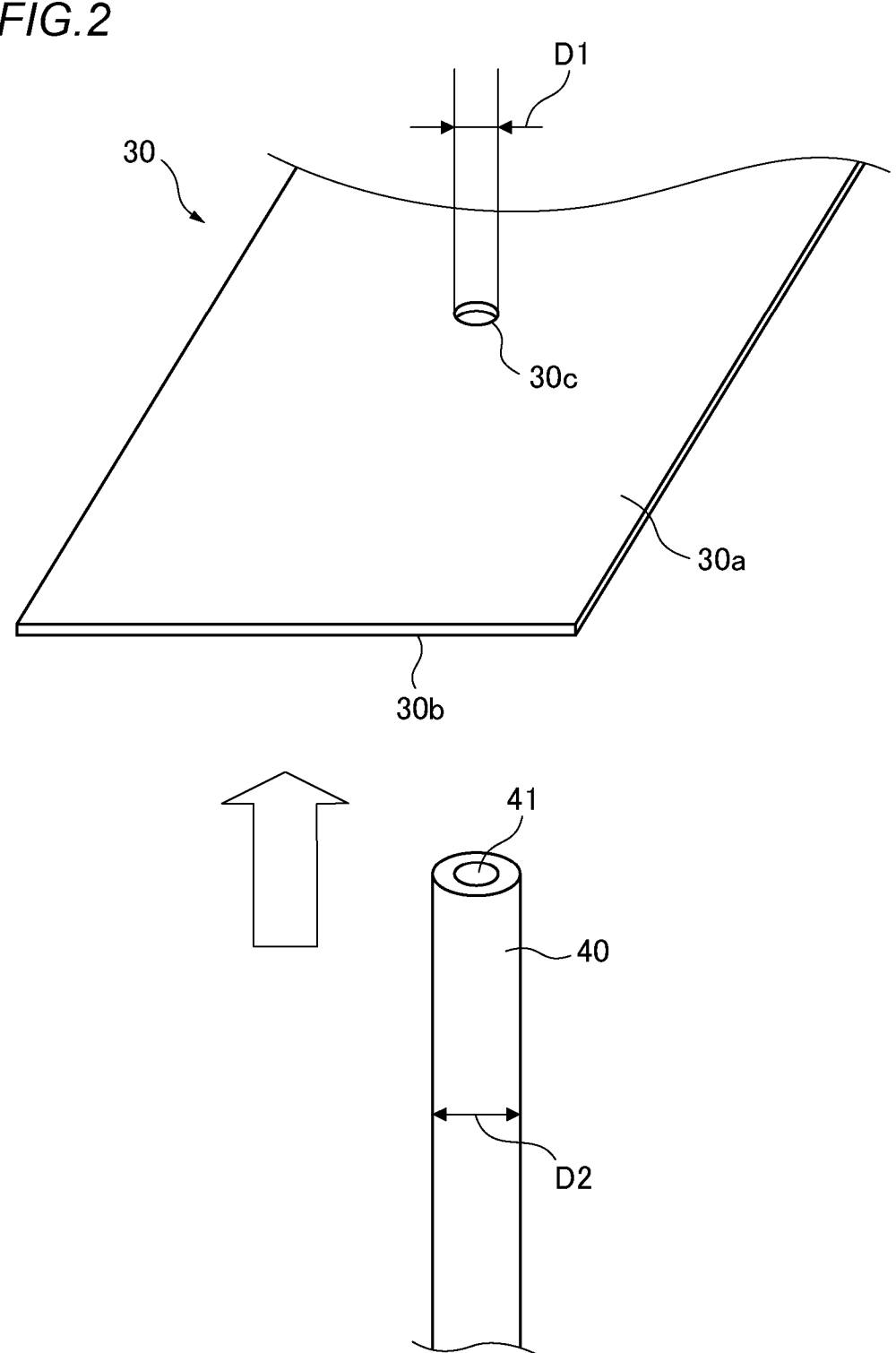
FIG. 2 illustrates a method of manufacturing the cuff.

First, as illustrated in FIG. 2, a sheet member 30 for forming the bladder 3 and a tubular member 40 for forming the ventilation tube 4 are prepared. The sheet member 30 has an upper surface $30a$ and a lower surface $30b$. A through hole $30c$ is formed in the sheet member 30. The through hole $30c$ communicates the upper surface $30a$ and the lower surface $30b$. A diameter D1 of the through hole $30c$ is smaller than an outer diameter D2 of the tubular member 40.

The tubular member 40 is placed so as to face either the upper surface $30a$ or the lower surface $30b$ of the sheet member 30. In the illustrated example, the tubular member 40 is placed so as to face the lower surface $30b$.

Figure 3:
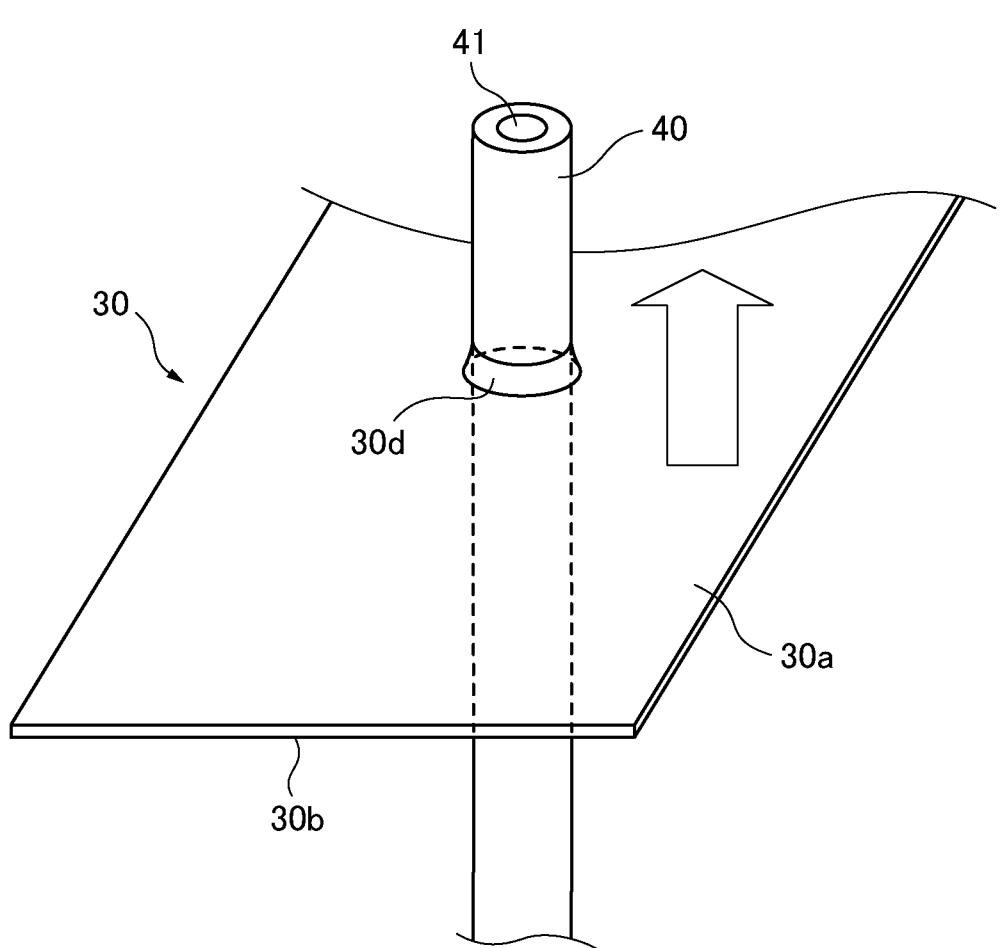
FIG. 3 illustrates the method of manufacturing the cuff.

Subsequently, as illustrated in FIG. 3, the tubular member 40 is inserted through the through hole $30c$ of the sheet member 30. In the illustrated example, the tubular member 40 passes through the through hole $30c$ from the side of the lower surface $30b$ to the side of the upper surface $30a$.

Figure 4A:
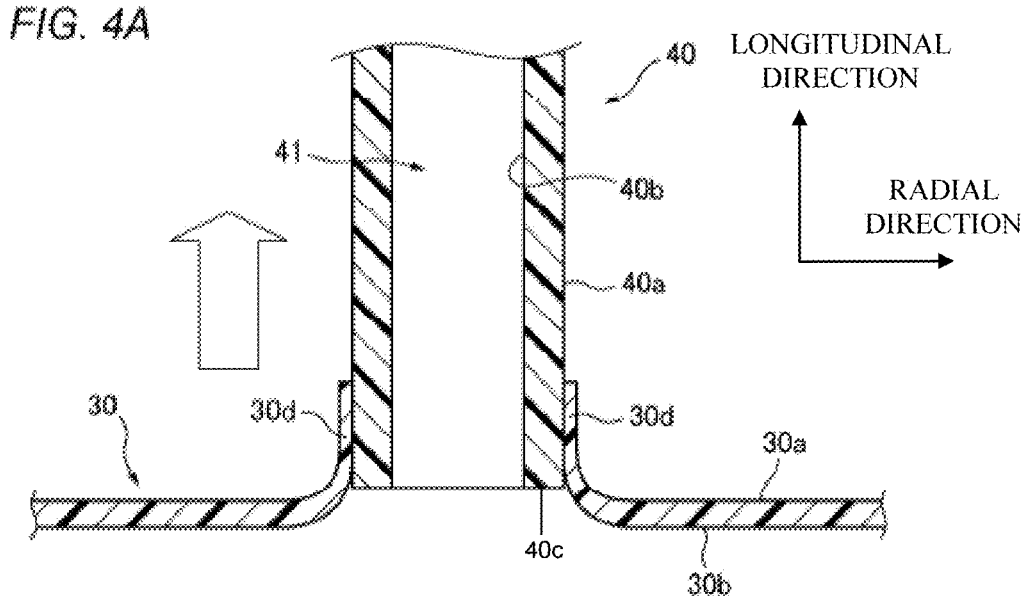
FIG. 4A illustrates the method of manufacturing the cuff.

Since the outer diameter D2 of the tubular member 40 is larger than the diameter D1 of the through hole $30c$, as illustrated in FIG. 4A, a peripheral portion of the through hole 30c in the sheet member 30 is pulled upward by an outer peripheral surface 40a of the tubular member 40, and a portion 30d extending along the longitudinal direction of the tubular member 40 is formed. The portion 30d is formed over the entire circumference of the tubular member 40. The tubular member has an end 40c that is closer to the bladder 3.

Figure 4B:
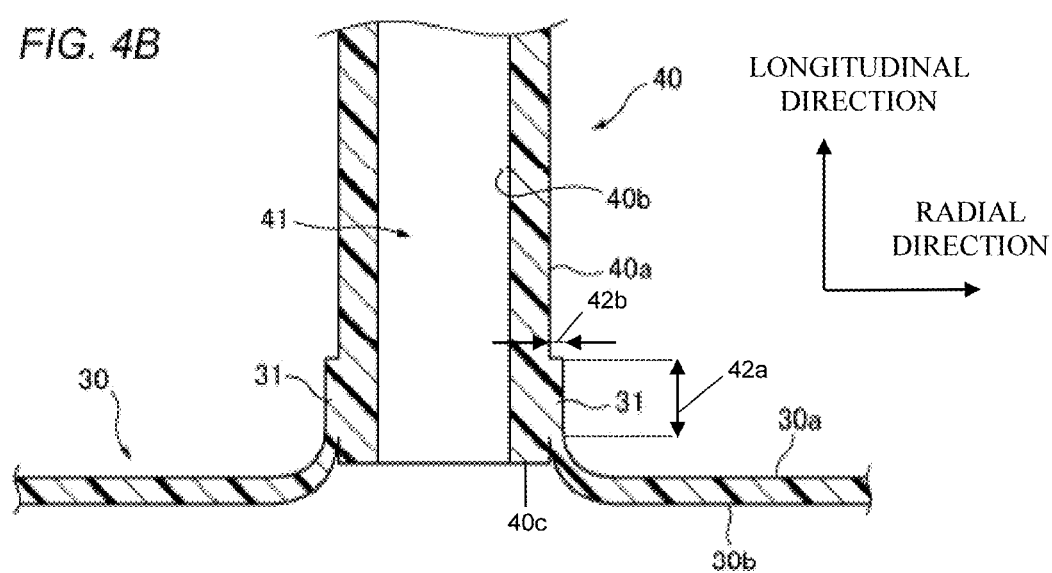
FIG. 4B illustrates the method of manufacturing the cuff.

Subsequently, as illustrated in the FIG. 4B, the portion 30d of the sheet member 30 is welded to the outer peripheral surface 40a of the tubular member 40. The welding is performed by a well-known technique such as high-frequency welding, laser welding, or thermal welding. As a result, the first welded portion 31 in which a portion of the sheet member 30 and a portion of the tubular member 40 are made integrally indivisible is formed. Therefore, the first welded portion 31 extends along the longitudinal direction of the tubular member 40 over the entire circumference of the tubular member 40.

Figure 5A:
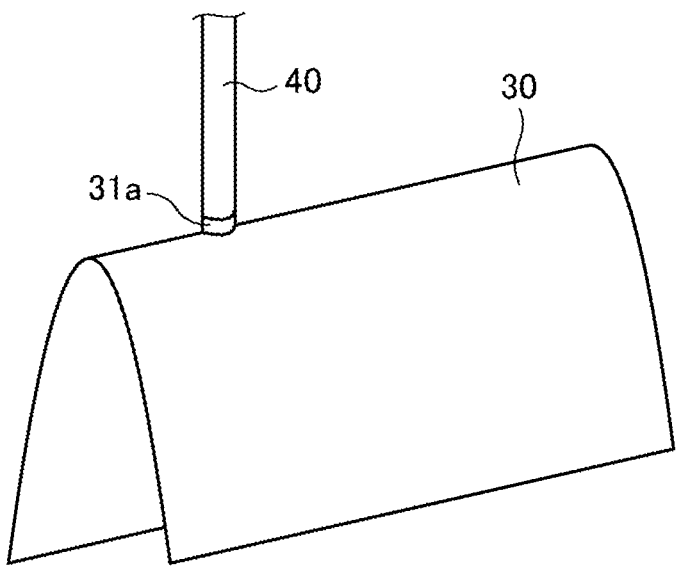
FIG. 5A illustrates the method of manufacturing the cuff.

Subsequently, as illustrated in the FIG. 5A, the sheet member 30 to which the tubular member 40 is welded is deformed into an appropriate shape for forming the bladder 3.

Figure 5B:
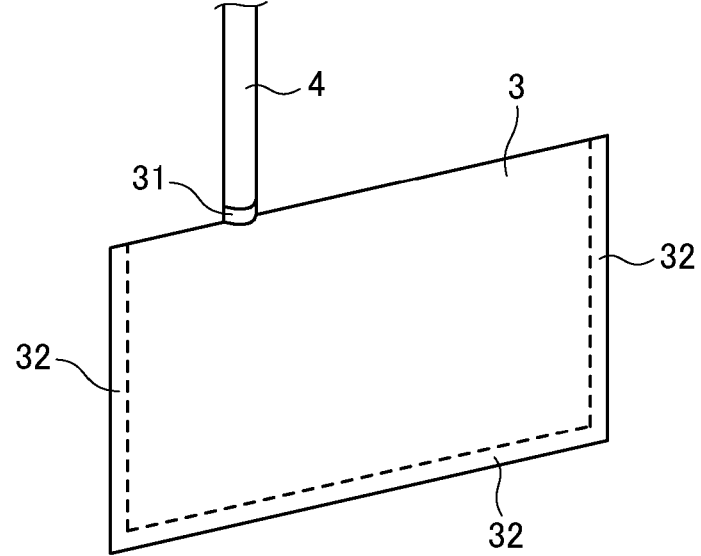
FIG. 5B illustrates the method of manufacturing the cuff.

Further, as illustrated in the FIG. 5B, different portions of the sheet member 30 are welded to each other. The welding is performed by a well-known technique such as high-frequency welding, laser welding, or thermal welding. As a result, the second welded portion 32 in which the different portions of the sheet member 30 are integrally indivisible is formed. The different portions of the sheet member 30 to be welded are selected so that the second welded portion 32 is formed at a position separated from the first welded portion 31.

The bladder 3 having airtightness is defined by the first welded portion 31 and the second welded portion 32. The tubular member 40 is subjected to an appropriate treatment to form the ventilation tube 4. The cuff 1 illustrated in the FIG. 1A is obtained by incorporating the bladder 3 formed as described above into the cuff 2.

The manufacturing method as described above and the cuff 1 obtained by the manufacturing method have the following advantages.

When the welded portion is formed by a flange portion like the nozzle in the cuff described in PTL1, such a welded portion extends on the inner surface of the bladder along the radial direction of the ventilation tube. According to the configuration of the present embodiment, since the formation of such a flange portion is unnecessary, the first welded portion 31 does not have a portion extending along the radial direction of the ventilation tube 4. In other words, the first welded portion 31 has a negligible size as compared with a portion extending along the longitudinal direction of the ventilation tube 4. Therefore, it is possible to suppress a decrease in flexibility at the joint portion between the bladder 3 and the ventilation tube 4. As a result, the close contactability between the surface of the cuff 1 and the body surface of the subject can be improved, which can contribute to an improvement in the accuracy of blood pressure measurement.

The second welded portion 32 is formed by welding different portions of the sheet member 30 in a plane orthogonal to the longitudinal direction of the tubular member 40. In other words, the second welded portion 32 has a large thickness dimension in the plane orthogonal to the longitudinal direction of the tubular member 40, and thus has low flexibility. Since the second welded portion 32 is separated from the first welded portion 31 forming the joint portion between the sheet member 30 and the tubular member 40, the influence of the rigidity of the second welded portion 32 on the flexibility of the joint portion can be suppressed. That is, the flexibility of the joint portion between the bladder 3 and the ventilation tube 4 does not have a direction dependence in the plane orthogonal to the longitudinal direction of the ventilation tube 4. As a result, the degree of freedom of deformation at the joint portion between the bladder 3 and the ventilation tube 4 is improved. Therefore, the close contactability between the surface of the cuff 1 and the body surface of the subject can be improved, which can contribute to the improvement of the accuracy of the blood pressure measurement.

In order to manufacture a component having a flange portion such as the nozzle in the cuff described in PTL1, injection molding is necessary. On the other hand, since the tubular member 40 according to the present embodiment does not have such a flange portion, it can be manufactured by extrusion molding. Since the extrusion molding is a lower-cost method than the injection molding, an increase in the manufacturing cost of the cuff 1 can be suppressed.

The material of the tubular member 40 is preferably selected to contain the same material as the sheet member 30. In this case, the welding strength can be considerably increased.

In the above embodiment, the first welded portion 31 is formed by welding the sheet member 30 to the outer peripheral surface 40a of the tubular member 40. However, the first welded portion 31 may also be formed by welding the sheet member 30 to an inner peripheral surface 40b of the tubular member 40.

In this instance, as illustrated in the FIG. 6A, the tubular member 40 is placed on the side facing the upper surface 30a of the sheet member 30. The side facing the upper surface 30a is an example of the first side of the sheet member. The tubular member 40 defines a ventilation channel 41 having an inner diameter D3 larger than the diameter D1 of the through hole 30c.

Subsequently, a peripheral portion 30e of the through hole 30c in the sheet member 30 illustrated in the FIG. 6A is pushed into the ventilation channel 41 from the side facing the lower surface 30b of the sheet member 30. The side facing the lower surface 30b is an example of the second side of the sheet member. As a result, as illustrated in the FIG. 6B, a section 30f extending along the length of the tubular member 40 is formed. The portion 30f is formed around the entire circumference of the tubular member 40.

Figure 6C:
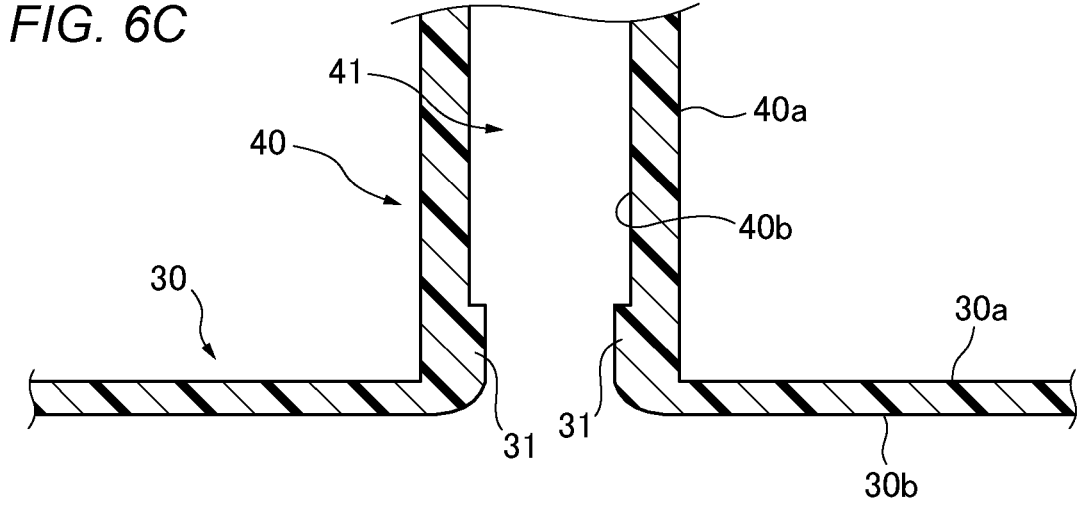
FIG. 6C illustrates another method of manufacturing the cuff

Subsequently, as illustrated in the FIG. 6C, a portion 30f of the sheet member 30 is welded to the inner peripheral surface 40b of the tubular member 40. The welding is performed by a well-known technique such as high-frequency welding, laser welding, or thermal welding. As a result, the first welded portion 31 in which a portion of the sheet member 30 and a portion of the tubular member 40 are made integrally indivisible is formed. Therefore, the first welded portion 31 extends along the longitudinal direction of the tubular member 40 over the entire circumference of the tubular member 40.

The subsequent steps are the same as those of the embodiment described above with reference to FIG. 5. Therefore, also in this example, the first welded portion 31 and the second welded portion 32 are separated from each other.

The above embodiment is merely exemplary to facilitate understanding of the presently disclosed subject matter. The configuration according to the above embodiment can be appropriately modified or improved without departing from the fundamental concept of the presently disclosed subject matter.

In the above embodiment, the second welded portion 32 is formed by welding different portions of the single sheet member 30. However, the second welded portion 32 may be formed by welding different portions of a plurality of sheet members. That is, the bladder 3 may be formed of at least one sheet member.

The present application is based on Japanese Patent Application No. 2019-015839 filed on Jan. 31, 2019, the entire contents of which are hereby incorporated by reference.

The invention claimed is:

1. A cuff adapted to be used for blood pressure measurement comprising:
  a sheet member forming a bladder;
  a tubular member forming a ventilation channel communicating with the bladder; and
  a welded portion at which the sheet member is welded to an outer circumferential surface of the tubular member,
  wherein the welded portion extends along a longitudinal direction of the tubular member over an entire circumference of the tubular member,
  wherein a dimension of the welded portion along the longitudinal direction of the tubular member is larger than a dimension of the welded portion along a radial direction of the tubular member; and
  wherein an inner surface of the sheet member is curved toward an end of the tubular member in the longitudinal direction of the outer circumferential surface that is closer to the bladder, and the inner surface of the sheet member is curved toward an exterior of the bladder.

2. The cuff according to claim 1, wherein the sheet member and the tubular member contain an identical material.

3. The cuff according to claim 1, wherein the sheet member forming the welded portion is a single sheet.

4. The cuff according to claim 1, wherein a diameter of the tubular member a fixed sizing at all points where the welded portion is formed.

5. A cuff adapted to be used for blood pressure measurement comprising:
  a sheet member forming a bladder;
  a tubular member forming a ventilation channel communicating with the bladder; and
  a welded portion at which the sheet member is welded to an inner circumferential surface of the tubular member,
  wherein the welded portion extends along a longitudinal direction of the tubular member over an entire circumference of the tubular member;
  wherein a dimension of the welded portion along the longitudinal direction of the tubular member is larger than a dimension of the welded portion along a radial direction of the tubular member; and
  wherein an end in the longitudinal direction of an outer circumferential surface of the tubular member that is closer to the bladder is located outside the bladder.

6. The cuff according to claim 5, wherein the sheet member and the tubular member contain an identical material.

7. The cuff according to claim 5, wherein the sheet member forming the welded portion is a single sheet.

* * * * *